United States Patent
Camras

[11] Patent Number: 5,346,464
[45] Date of Patent: Sep. 13, 1994

[54] METHOD AND APPARATUS FOR REDUCING INTRAOCULAR PRESSURE

[76] Inventor: Carl B. Camras, 10401 N. 108th St., Omaha, Nebr. 68142

[21] Appl. No.: 48,465

[22] Filed: Apr. 14, 1993

Related U.S. Application Data

[63] Continuation-in-part of Ser. No. 848,916, Mar. 10, 1992, abandoned.

[51] Int. Cl.⁵ .............................................. A61M 5/00
[52] U.S. Cl. ........................................ 604/9; 604/8; 604/294
[58] Field of Search ................. 604/8, 9, 10, 265, 266, 604/294, 30, 31, 34

[56] References Cited

U.S. PATENT DOCUMENTS

| | | | |
|---|---|---|---|
| 3,654,932 | 4/1972 | Newkirk et al. | 604/9 |
| 4,037,604 | 7/1977 | Newkirk | 128/350 |
| 4,464,168 | 8/1984 | Redmond et al. | 604/9 |
| 4,554,918 | 11/1985 | White | 604/10 |
| 4,560,375 | 12/1985 | Schulte et al. | 609/9 |
| 4,605,395 | 8/1986 | Rose et al. | 604/9 |
| 4,729,761 | 3/1988 | White | 604/8 |
| 4,741,730 | 5/1988 | Dormandy, Jr. et al. | 604/9 X |
| 4,886,488 | 12/1989 | White | 604/9 |
| 5,073,163 | 12/1991 | Lippman | 604/9 |

OTHER PUBLICATIONS

*Ophthalmology*–"A Long Krupin–Denver valve Implant Attached to a 180° Scleral Explant for Glaucoma Surgery"–vol. 95, No. 9, Sep. 1988.
*New Ideas*–"A Temporary Glaucoma Valve For Transient Intraocular Pressure Elevation"–Marino Blasini, M. Bruce Shields, Dyson Hickingbotham–Mar. 1990, vol. 21, No. 3.

*Primary Examiner*—Robert A. Hafer
*Assistant Examiner*—Sam Rimell
*Attorney, Agent, or Firm*—Zarley, McKee, Thomte, Voorhees & Sease

[57] ABSTRACT

An apparatus for reducing intraocular pressure includes first and second resilient flexible tubes connected together to permit fluid flow therethrough. The first tube has one end inserted within the anterior chamber of the eye to drain fluid therefrom and extends through an aperture in the conjunctival layer. The second tube is connected to the external end of the first tube, and has an operable valve at the free end thereof which opens when subjected to a predetermined fluid pressure, to thereby reduce the intraocular pressure of the eye. A filter is mounted within the second tube to prevent bacteria from entering the anterior chamber of the eye, while permitting replacement of the filter as desired. A method for reducing intraocular pressure includes the step of inserting a first end of the first described tube into the anterior chamber of the eye, and positioning the second end external to the ocular surface of the eye. The second end of the tube is passed through an aperture in the conjunctival layer, so as to be positioned external to the ocular surface of the eye. The second tube is then connected to the first tube with the operable valve preferably located in the conjunctival cul-de-sac.

8 Claims, 2 Drawing Sheets

METHOD AND APPARATUS FOR REDUCING INTRAOCULAR PRESSURE

CROSS-REFERENCE TO RELATED APPLICATION

This is a continuation-in-part application of Ser. No. 07/848,916 filed Mar. 10, 1992, now abandoned.

TECHNICAL FIELD

The present invention relates generally to a procedure for reducing intraocular pressure in the eye utilizing a tubular shunt, and more particularly to an improved procedure and apparatus for draining aqueous fluid from the anterior chamber of the eye.

BACKGROUND OF THE INVENTION

Glaucoma is a disease of the eye characterized by damage to the optic nerve caused by intraocular pressure which is too high for the nerve to tolerate. Two types of procedures have generally been utilized in the prior art to control glaucoma: (1) decreasing aqueous fluid production and (2) increasing outflow of aqueous fluid from the anterior chamber of the eye. Of the numerous surgical procedures which have been described to control glaucoma, those which result in an improvement of outflow facility are theoretically more advantageous than those designed to decrease aqueous production, since over 95% of glaucomatous disease is a consequence of increased outflow resistance, rather than increased aqueous production or episcleral venous pressure. Operations designed to lower intraocular pressure by decreasing aqueous production have the disadvantage of curtailing aqueous flow to various avascular ocular structures which depend on nutrients supplied by aqueous humor for normal functioning.

The most frequently performed operation for chronic open angle glaucoma in adults is a "filtration" procedure which increases the outflow facility by providing an opening between the anterior chamber and subconjunctival space (between the conjunctiva and sclera) through which aqueous humor can flow to reduce intraocular pressure. The intraocular pressure level following these procedures varies, with an initial overfunction and its associated periods of low intraocular pressure (hypotony). The most common reason for failure of this type of glaucoma eye surgery is due to scarring in the subconjunctival space, thereby restricting the drainage flow from the anterior chamber.

A relatively new type of glaucoma surgery utilizes a valve implant, as disclosed in U.S. Pat. No. 4,037,604 to John Newkirk. The Newkirk device provides a tube which communicates between the anterior chamber of the eye and the subconjunctival space. The implant has a unidirectional valve at the end of a tube which is intended to open at a predetermined intraocular pressure, to release aqueous humor from the anterior chamber of the eye, to thereby reduce intraocular pressure. The open end of the tube is placed into the anterior chamber of the eye, while the valve end of the tube is located in the space between the sclera and the conjunctival tissues.

However, the Newkirk device still suffers failures since the valve implant does not reduce the incidence of scarring of the conjunctival, Tenon's, and/or episcleral tissue to the underlying sclera. Such failures may occur at any time in the post-operative course.

In a series of 79 eyes treated for neovascular glaucoma with the Newkirk apparatus, 53 eyes maintained an intraocular pressure less than or equal to 24 mm Hg with a mean follow-up of two years. Of these 53 "successfully" treated eyes, 10 eyes required bleb (the area in the subconjunctival space to which aqueous humor drains) revision because of scarring in the subconjunctival space with resultant increased intraocular pressure, which occurred between one and eleven months post-operatively. Of the 26 eyes which failed to maintain an intraocular pressure less than or equal to 24 mm Hg, 18 of the failures were secondary to bleb scarring, which occurred from three weeks to twenty months post-operatively. Even after attempted bleb revision in 8 of these 18 eyes, functional filtration could not be restored. Therefore, scarring of the conjunctival bleb resulted in permanent failure, or temporary failure requiring additional surgical intervention, in 28 of 79 eyes. Growth of fibrovascular tissue over the internal portion of the valve implant was responsible for failure in 10 of the eyes in this series.

In an attempt to eliminate bleb scarring, the tube was lengthened and a large Silastic disk was incorporated around the valve, thereby diverting drainage to a more posterior aspect of the eye, and spreading the drainage to a larger area. While this apparatus reduced failure due to bleb scarring, the scarring was not eliminated. Thus, prior art apparatus and procedures were not capable of accurately predicting or setting optimal intraocular pressures in the eye, since it was impossible to predict the amount of scarring and flow resistance in the bleb wall.

While many different forms of medical therapy have been used in an attempt to prevent the scarring of conjunctival, Tenon's and/or episcleral tissue over a drainage site, none have been shown to achieve 100% success, and all are associated with adverse effects.

SUMMARY OF THE INVENTION

It is therefore a general object of the present invention to provide an improved procedure for draining aqueous fluid from the anterior chamber of an eye which eliminates the possibility of scarring of conjunctival, Tenon's, and/or episcleral tissue over the external drainage site.

Another object of the present invention is to provide an apparatus for draining aqueous fluid from the anterior chamber of an eye which permits prediction and setting of optimal intraocular pressures.

Yet another object of the present invention is to provide a drainage apparatus with a controllable opening and closing pressure.

Still another object is to provide a drainage apparatus with a replaceable filter portion.

These and other objects of the present invention will be obvious to those of ordinary skill in the art.

The apparatus for reducing intraocular pressure of the present invention includes first and second resilient flexible tubes connected together to permit fluid flow therethrough. The first tube has one end inserted within the anterior chamber of the eye to drain fluid therefrom. The first tube extends through an aperture in the conjunctival layer, so as to be positioned externally of the ocular surface of the eye. The second tube is connected to the external end of the first tube, and has an operable valve at the free end thereof which opens when subjected to a predetermined fluid pressure, to thereby reduce the intraocular pressure of the eye. A filter is mounted within the second tube to prevent bacteria from entering the anterior chamber of the eye, while permitting replacement of the filter as desired. A method for reducing intraocular pressure includes the step of inserting a first end of the first described tube into the anterior chamber of the eye, and positioning the second end external to the ocular surface of the eye. Preferably, a portion of the sclera tissue of the eve adjacent the limbus is exposed, and the tube is inserted through an aperture in the limbus into the anterior chamber of the eye. The second end of the tube is passed through an aperture in the conjunctival layer, so as to be positioned external to the ocular surface of the eye. The second tube is then connected the first tube with the operable valve preferably located in the conjunctival cul-de-sac.

DESCRIPTION OF THE PREFERRED EMBODIMENT

Figure 1:
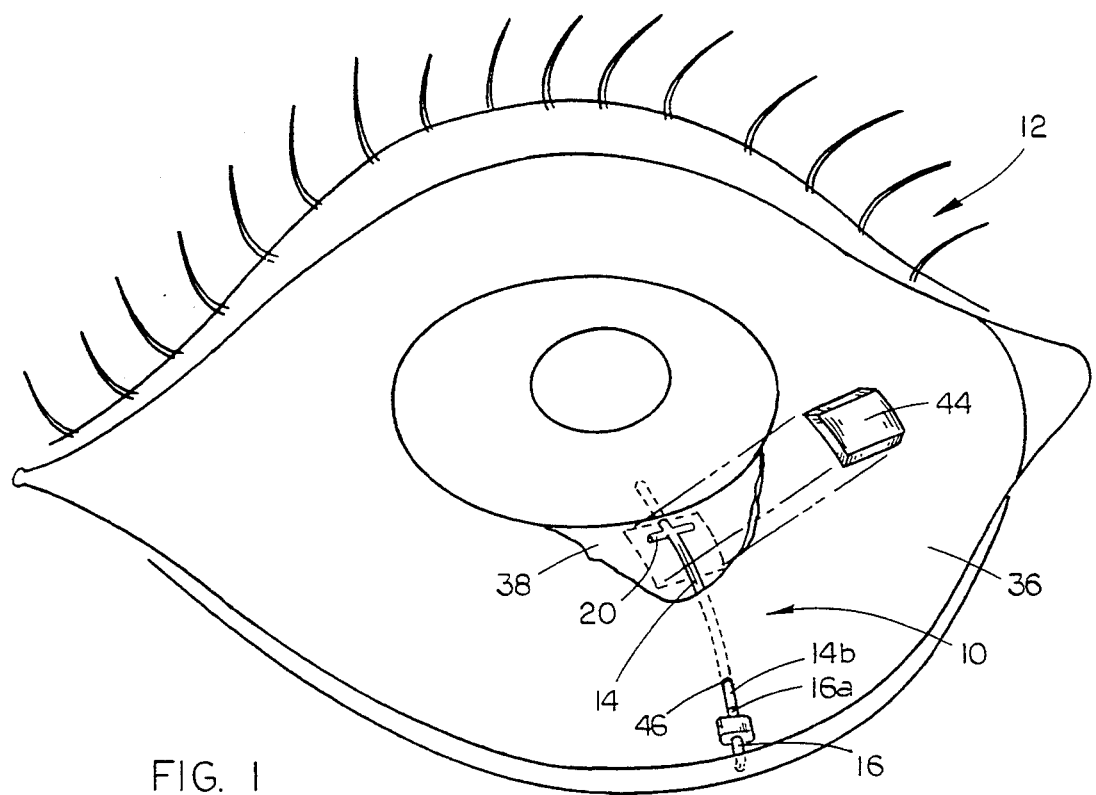
FIG. 1 is an enlarged pictorial view of an eye with the drainage apparatus of the present invention positioned for use.

Referring now to the drawings, in which similar or corresponding parts are identified with the same reference numerals, and more particularly to FIG. 1, the drainage apparatus of the present invention is designated generally at 10, and is shown installed in an eye 12.

Figure 2:
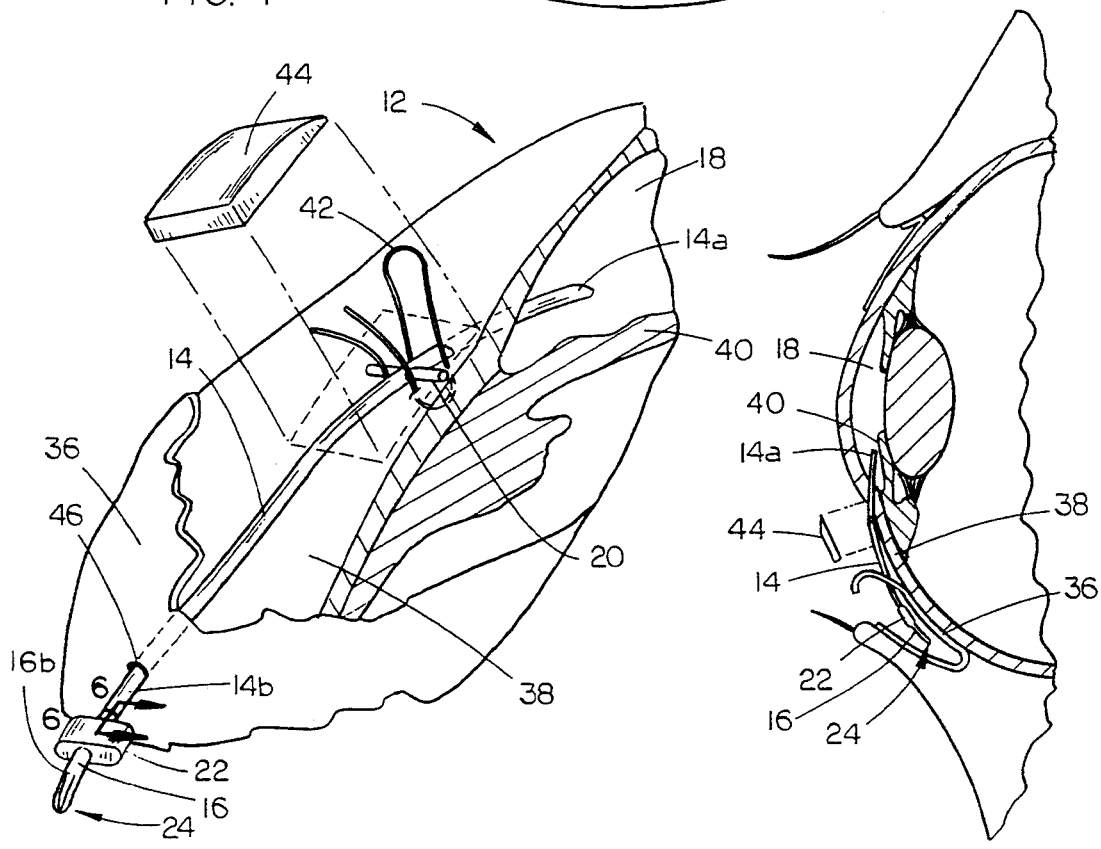
FIG. 2 is an enlarged perspective view of the drainage apparatus, showing the installation of the internal end of the apparatus.
Figure 6:
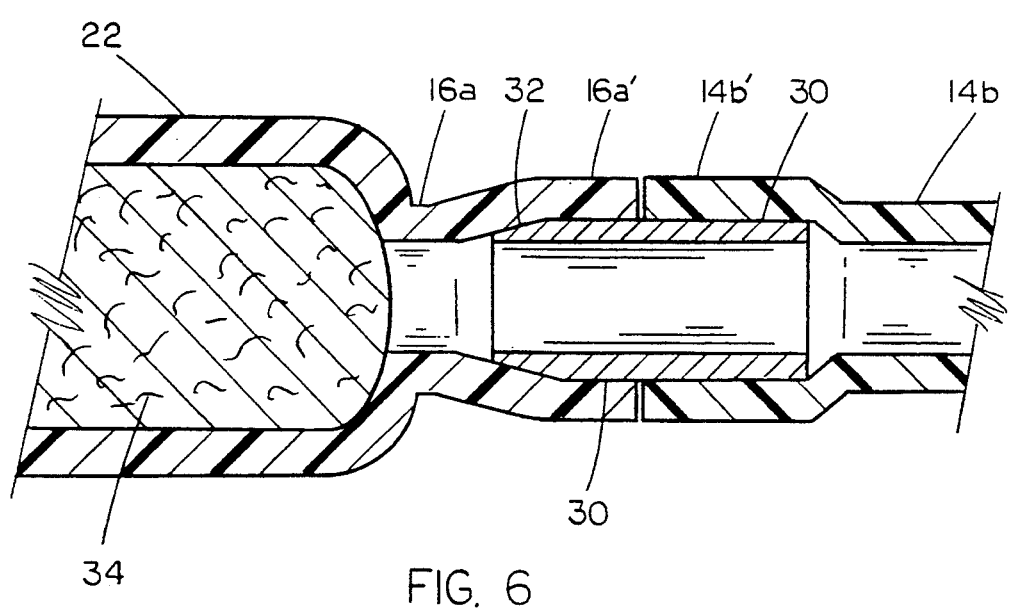
FIG. 6 is an enlarged sectional view taken at lines 6—6 in FIG. 2.

Drainage apparatus 10 is formed from a pair of coaxially interconnected tubes 14 and 16, the upper end 16a of lower tube 16 connected to the lower end 14b of upper tube 14, as shown FIG. 6. Referring now to FIG. 2, upper tube 14 is formed of a generally soft resilient flexible material and includes a generally diagonally cut internal upper end 14a which inserted into the anterior chamber 18 of eye 12 as described in more detail below. A cross-arm 2 0 is affixed to upper tube 14 for use in suturing tube 14 to eye 12, again described below.

Figure 4:
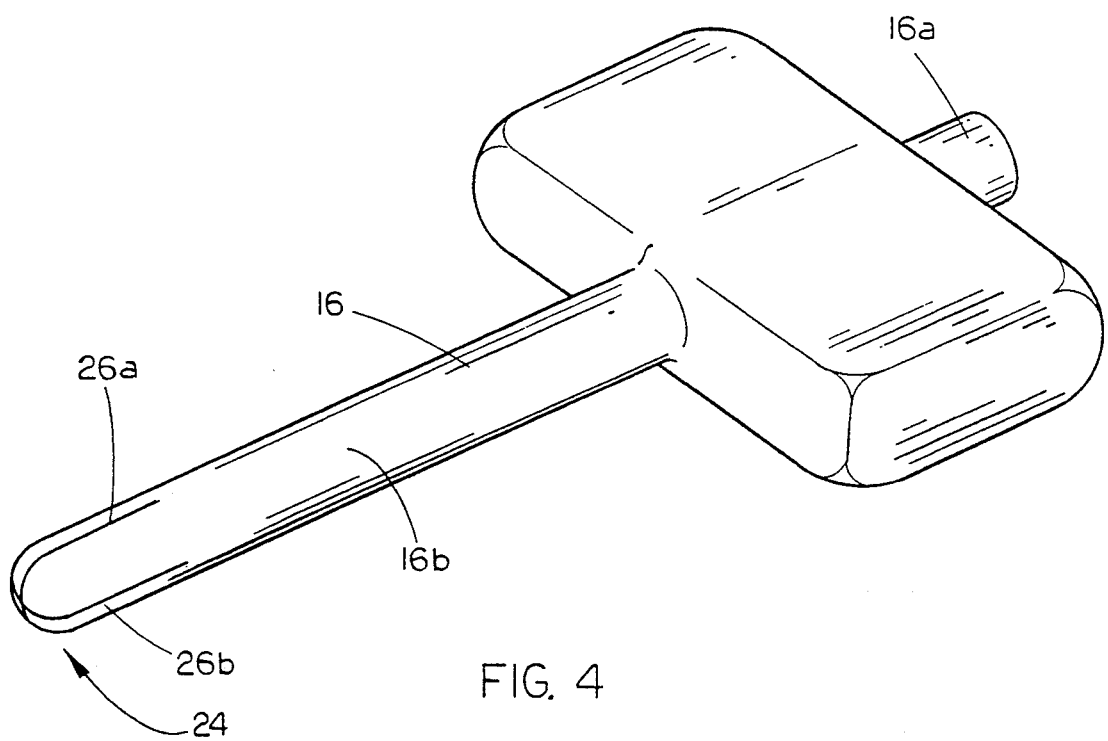
FIG. 4 is a super enlarged perspective view of the replaceable lower section of the apparatus.
Figure 5:
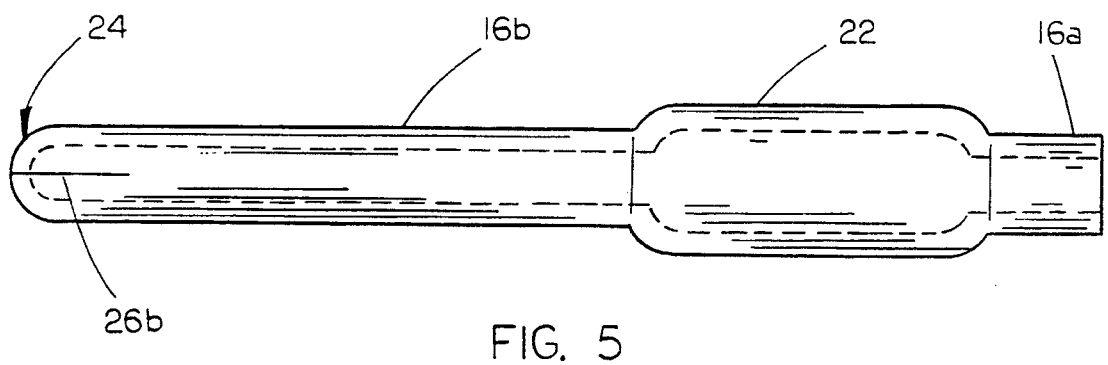
FIG. 5 is a side elevational view of the apparatus of FIG. 4.

Referring now to FIGS. 4–6, lower tube 16 is an elongated tube of generally soft resilient flexible material with an enlarged filter chamber 22 formed therein. The lower end 16b is closed, but includes a unidirectional valve 24 formed by a pair of cross slits 26a and 26b, which extend upwardly a short distance through the wall of tube 16.

Referring now to FIG. 6, the lower end 14b of upper tube 14 and the upper end 16a of lower tube 16 have the same interior and exterior diameters. A sleeve 30 of rigid material has an inner diameter equal to the interior diameters of tube ends 14b and 16a, and is inserted in the tube ends to connect them together. Because tubes 14 and 16 are formed of a flexible resilient material, lower end 14b of upper tube 14 has a portion 14b' which is expanded in diameter to receive one-half of sleeve 30 therein. Similarly, upper end 16a of lower tube 16 has a portion 16a' which is expanded in diameter to receive the opposite half of sleeve 30 therein, with ends 16a' and 14b' preferably in abutting contact on sleeve 30. Thus, ends 14b' and 16a' are stretched in diameter slightly for a press fit connection retaining tubes 14 and 16 on connector sleeve 30. A beveled portion 32 is formed on the outer wall of the lower end of sleeve 30, to enable lower tube 16 to be more easily press fit onto sleeve 30.

A polycarbonate capillary filter 34 is secured within filter chamber 22, and preferably has a pore diameter of approximately 0.22 microns. In order to allow adequate flow of aqueous humor, the surface area required for a filter with this pore diameter is approximately 1.5 mm$^2$ (dimensions of approximately 0.6 mm by 2.5 mm). However, more critically, the filter 34 must extend throughout the entire height and width of chamber 22 such that aqueous humor must pass through the filter to continue to lower end 16b of tube 16. Filter 34 will permit outflow of aqueous humor at a rate of approximately 3.6 microliters per minute at an intraocular pressure of approximately 10 mm Hg. In this way, filter 34 will not result in any additional impedance to outflow, which will be controlled by valve 24 at lower end 16b of tube 16.

The procedure for installing drainage apparatus 10 includes the initial step of performing a peritomy to disconnect a fornix-based flap of conjunctival and Tenon's tissue 36 from the limbus extending approximately 6 mm, leaving bare sclera 38. Internal end 14a of tube 14 is inserted through the limbus approximately 3 mm into the anterior chamber 18, parallel to the iris plane 40. Tube 14 is then secured in position with suture 42 which is tied around cross-arm 20 and into the sclera tissue 38, so as to stabilize tube 14 and prevent posterior migration. Additional sutures may be used to further secure the tube to the sclera.

A portion of tube 14 which extends from the limbus, is covered with a donor scleral patch graft 44 of about 5 mm in length. The lower end 14b of tube 14 is passed through an aperture 46 in the conjunctiva 36 utilizing an angiocatheter technique, wherein a trocar within the lumen of a catheter is utilized to pierce the conjunctiva and is withdrawn to leave the catheter in place. The external end 14b of tube 14 is then passed through the catheter (and thereby through the conjunctiva 36). The catheter is then withdrawn from aperture 46 so as to leave tube 14 in position through aperture 46.

Lower tube 16 is then connected to the lower end of tube 14 such that lower tube 16 remains completely external of eye 12. Depending upon the tightness of the fit between the connector sleeve 30 and adjoining tube ends 14b and 16a, it may be necessary to utilize a separate instrument to expand the tube ends to assist in connecting the tube ends to sleeve 30.

Figure 3:
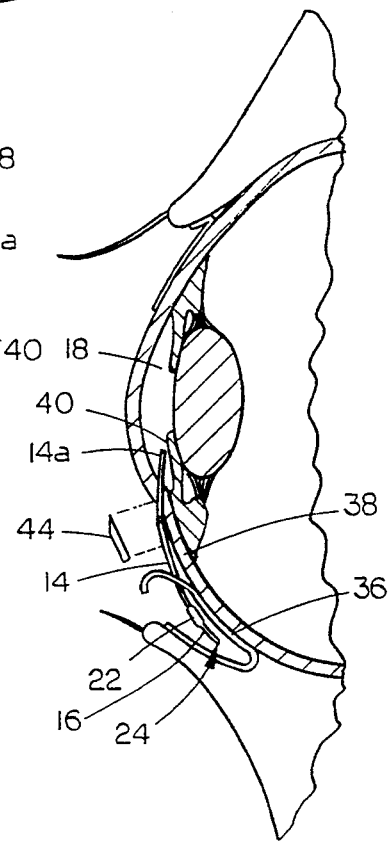
FIG. 3 is a cross-sectional view through an eye with the drainage apparatus installed therein.

Preferably, valve 24 is located between the papebral and bulbar conjunctiva close to, or within, the cul-de-sac, as shown in FIG. 3. Thus, drainage apparatus 10 extends from anterior chamber 18 to the external ocular surface of eye 12.

A prototype of an early version of drainage apparatus 10, which used a permanent filter, was implanted in one eye each of three cynomolgus monkeys with bilateral argon laser-induced glaucoma. The contralateral control eyes underwent standard trabeculectomies. Preoperative intraocular pressures were greater than 25 mm Hg in all eyes. Post-operative intraocular pressures were maintained at less than or equal to 20 mm Hg in all three eyes with the apparatus 10 of the present invention, but rose to greater than 20 mm Hg within one to four weeks in the three control eyes. Pseudomonas aeruginosa was repeatedly applied to the external portion of apparatus 10 in two eyes without producing a Pseudomonas endophthalmitis, whereas the same strains injected into rabbit eyes produced fulminant endophthalmitis within hours.

These initial test results support the contention that a valved anterior chamber tubular shunt to the external ocular surface can have beneficial results in glaucomatous primate eyes. The shunting of fluid to the exterior ocular surface eliminates the scarring which has caused failure of prior art devices which shunted fluid to the subconjunctival space. The use of a filter mounted within the tube prevents the entry of bacteria into the anterior chamber.

Whereas the method and apparatus of the present invention has been shown and described in connection with the preferred embodiment thereof, it will be understood that many modifications, substitutions and additions may be made which are within the intended broad scope of the appended claims. There has therefore been shown and described an improved method and apparatus for draining aqueous fluid from the anterior chamber of the eye, which accomplishes at least all of the above stated objects.

I claim:

1. A surgical procedure for reducing intraocular pressure within an eye, the eye including an anterior chamber with aqueous humor under pressure therein, a cornea and surrounding marginal limbus by which the cornea is continuous with a layer of scleral tissue covered by a layer of conjunctival tissue, the conjunctival tissue forming a cul-de-sac around the periphery of the forward external surface of the eye and under the eyelids, said procedure including the steps of:
   providing a tubular shunt having first and second coaxially and removably connected tubes, having a length to extend from within the anterior chamber to a portion of the conjunctival cul-de-sac, the first tube having first and second ends and the second tube having first and second ends, with a filter mounted within said second tube to prevent bacterial ingress;
   inserting the first end of the first tube into the anterior chamber;
   piercing the conjunctival layer and passing the second end of the first tube outwardly therethrough to lay externally of the conjunctival layer;
   connecting the first end of the second tube to the second end the first tube such that said second tube lays externally of the conjunctival layer.

2. The procedure of claim 1, further comprising the steps of:
   exposing an area of scleral tissue immediately adjacent the limbus, immediately prior to the step of inserting the first end of the first tube;
   said step of inserting the first end of the first tube, including the step of piercing the limbus anterior to the exposed scleral area and inserting the first end of the first tube therethrough; and
   securing a portion of the first tube to the scleral tissue the exposed area.

3. The procedure of claim 2, wherein the step of exposing an area of scleral tissue includes the steps of:
   disconnecting the conjunctival layer along a portion of the limbus and relaxing the conjunctival layer to expose an area of scleral tissue; and
   reconnecting the conjunctival layer along the limbus after the step of passing the second end of the first tube through the conjunctival layer.

4. The procedure of claim 2, wherein the step of piercing the conjunctival layer includes the step of piercing the conjunctival layer at a location adjacent and spaced from the exposed scleral tissue.

5. The procedure of claim 1, wherein the step of connecting the first end of the second tube to the second end of the first tube includes the step of locating the second end of the second tube in the conjunctival cul-de-sac.

6. The surgical procedure of claim 2, further comprising the steps of:
   covering that portion of the first tube which extends from the limbus to the conjunctival layer, with a scleral patch graft; and
   securing the scleral patch graft to the surface of the scleral tissue.

7. The surgical procedure of claim 1, wherein said eye includes an iris, and wherein the step of piercing the limbus and inserting the first end of the first tube includes the step inserting and positioning the first end of the first tube generally parallel to the iris plane.

8. The surgical procedure of claim 1, further comprising the steps of:
   disconnecting the second tube from the first tube after a period of time;
   providing a replacement second tube having first and second ends and a filter therein to prevent bacterial ingress; and
   connecting the first end of the replacement second tube to the second end of the first tube and laying the second end the replacement tube externally of the conjunctival layer.

* * * * *